United States Patent
Layman et al.

(10) Patent No.: US 8,350,074 B2
(45) Date of Patent: Jan. 8, 2013

(54) LOW TRIPHENYLPHOSPHATE, HIGH PHOSPHOROUS CONTENT ISOPROPYL PHENYL PHOSPHATES WITH HIGH ORTHO ALKYLATION

(75) Inventors: William J. Layman, Baton Rouge, LA (US); Arthur G. Mack, Prairieville, LA (US); Techen Tsao, Stafford, TX (US); Jeffrey Todd Aplin, Baton Rouge, LA (US); Hoover Chew, Summerville, SC (US); Douglas W. Luther, Walker, LA (US)

(73) Assignee: Albemarle Corporation, Baton Rouge, LA (US)

( * ) Notice: Subject to any disclaimer, the term of this patent is extended or adjusted under 35 U.S.C. 154(b) by 0 days.

(21) Appl. No.: 13/232,388

(22) Filed: Sep. 14, 2011

(65) Prior Publication Data

US 2012/0004438 A1  Jan. 5, 2012

Related U.S. Application Data

(62) Division of application No. 12/297,273, filed as application No. PCT/US2007/067188 on Apr. 23, 2007, now Pat. No. 8,143,433.

(60) Provisional application No. 60/794,785, filed on Apr. 24, 2006, provisional application No. 60/908,287, filed on Mar. 27, 2007, provisional application No. 60/908,292, filed on Mar. 27, 2007.

(51) Int. Cl.
*C07F 9/09* (2006.01)
(52) U.S. Cl. ......................................................... 558/124
(58) Field of Classification Search ................... 558/124
See application file for complete search history.

(56) References Cited

U.S. PATENT DOCUMENTS

| | | | |
|---|---|---|---|
| 3,859,395 | A | 1/1975 | Terhune et al. |
| 4,069,279 | A | 1/1978 | Boyden |
| 4,093,680 | A | 6/1978 | Randell et al. |
| 4,139,487 | A | 2/1979 | Garrett |
| 4,370,281 | A | 1/1983 | Clubley et al. |
| 5,206,404 | A | 4/1993 | Gunkel et al. |
| 5,401,824 | A | 3/1995 | Clatty et al. |
| 5,624,968 | A | 4/1997 | Gabbard |
| 6,232,485 | B1 | 5/2001 | Derbyshire et al. |
| 6,242,631 | B1 | 6/2001 | Hombek et al. |

FOREIGN PATENT DOCUMENTS

| | | |
|---|---|---|
| CA | 930371 A | 7/1973 |
| EP | 0 324 716 A2 | 7/1989 |
| WO | 00/17210 A1 | 3/2000 |

*Primary Examiner* — Shawquia Young
(74) *Attorney, Agent, or Firm* — James A. Jubinsky

(57) ABSTRACT

The present invention relates to low triphenyl phosphate, high phosphorous content aryl phosphates with high ortho alkylation that are suitable for use as flame retardant compositions, processes for their preparation, and their use as flame retardants.

8 Claims, No Drawings

LOW TRIPHENYLPHOSPHATE, HIGH PHOSPHOROUS CONTENT ISOPROPYL PHENYL PHOSPHATES WITH HIGH ORTHO ALKYLATION

REFERENCE TO RELATED APPLICATIONS

This application is a division of pending U.S. patent application Ser. No. 12/297,273, filed Apr. 3, 2009, which application is the National Stage of International Patent Application No. PCT/US2007/067188, filed on Apr. 23, 2007, which, in turn, claims the benefit of U.S. Provisional Patent Application No. 60/794,785, filed Apr. 24, 2006; U.S. Provisional Patent Application No. 60/908,287, filed on Mar. 27, 2007, and U.S. Provisional Patent Application No. 60/908,292, filed on Mar. 27, 2007, the disclosures of which are incorporated herein by reference.

FIELD OF THE INVENTION

The present invention relates to flame retardant compositions and a process for their preparation. More particularly, the present invention relates to low triphenyl phosphate, high phosphorous content, aryl phosphates, with high ortho alkylation that are suitable for use as flame retardant compositions, and a process for their preparation.

BACKGROUND OF THE INVENTION

Alkylated aryl phosphates are known in the art to be useful as flame-retardants. These compounds can be formed by a number of methods commonly used in the art. For example, it is known to prepare mixed synthetic triaryl phosphates by alkylating phenol with alkenes such as propylene or isobutylene to obtain a mixture of phenol and substituted phenols. According to U.S. Pat. No. 4,093,680 this alkylate mixture is then reacted with phosphorus oxychloride ($POCl_3$) to form a mixed triaryl phosphate ester. The product mix is a statistical mixture based on the composition of the starting alkylates and always includes some fraction of triphenyl phosphates ("TPP"), usually from 5 to 50 percent. The product's physical properties are determined by the degree of alkylation of the phenol. A highly alkylated phenol mixture will result in a more viscous phosphate ester product than one less substituted.

Triphenyl phosphate is a by-product of the alkylated phenyl phosphate formation reaction and is unwanted in the final product because of environmental concerns. For example, TPP has been classified as a marine pollutant in some jurisdictions. Thus, there has been much attention in the art given to removing TPP from alkylated phenyl phosphates. For example, U.S. Pat. No. 5,206,404 discloses that wipe film purification can be used to produce mixed alkylated triphenyl phosphates with TPP concentrations of less than 2 wt %. The '404 patent also discloses that an undesirable method of reducing the TPP concentration of alkylated phenyl phosphates is by fractional distillation.

U.S. Pat. No. 6,232,485 discloses a process for producing a liquid triaryl phosphate ester having low triphenyl phosphate concentrations and low viscosity comprising (a) an alkylation stage wherein a phenol is reacted with an olefin having 2 to 12 carbon atoms in the presence of a strong acid catalyst to give a reaction product comprising a mixture of meta and para alkylated phenols; (b) a transalkylation stage wherein the mixture of alkylated phenols from the alkylation stage is heated in the presence of a strong acid catalyst to increase the meta isomer content of the mixture to at least 20% whilst maintaining a phenol level below 22%; and (c) a phosphorylation stage. In the '485 process, the mixture of alkylated phenols from the transalkylation stage is reacted with a phosphorylating agent, and the strong acid catalyst used in stages (a) and (b) is a Bronsted acid having an acid strength of less than zero.

However, none of the prior art processes are without drawbacks. For example, the '404 patent teaches that repeated passes through the wipe film evaporator may be necessary to reduce TPP concentrations to desired levels. Fractional distillation has also been taught as a method to reduce TPP concentrations in the final triaryl phosphate ester product, which also has drawbacks. As noted in the '404 patent, fractional distillation of the final triaryl phosphate ester product produces a product that has undesirable color and acidity levels. Likewise, the '485 patent, and others such as U.S. Pat. Nos. 4,069,279, 4,139,487 and 6,232,485 disclose processes that produce products comprising mixtures of alkylated phenyl phosphates with alkyl groups distributed on more than one phenyl group. These product distributions have undesirable properties such as high viscosity, inconsistent viscosity characteristics, and high triphenyl phosphate concentrations.

Thus, there exists a need in the art for low triphenyl phosphate, high phosphorous alkylated phenyl phosphates with high ortho alkylation, and a process for their formation.

SUMMARY OF THE INVENTION

In one embodiment, the present invention relates to an alkylated triaryl phosphate ester comprising less than about 1 wt % triphenyl phosphate, based on the total weight of the alkylated triaryl phosphate ester, and an organic phosphorous content in the range of from about 5 to about 10 wt %, based on the total weight of the alkylated triaryl phosphate ester.

In another embodiment, the present invention relates to an alkylated triaryl phosphate ester comprising one or more of the following alkylated phenyl phosphates: a) monoalkylphenyl diphenyl phosphates; b) di-(alkylphenyl)phenyl phosphates; c) dialkylphenyl diphenyl phosphates; d) trialkylphenyl phosphates; e) alkylphenyl dialkylphenyl phenyl phosphates; and less than about 1 wt. % triphenyl phosphate, based on the total weight of the alkylated triaryl phosphate ester, wherein the alkyl moieties of the alkylated phenyl phosphates are selected from methyl, ethyl, propyl, isopropyl, butyl, isobutyl, tertiary-butyl, amyl, isoamyl, tertiary-amyl, and cyclohexyl groups and the total phosphorous content of the alkylated triaryl phosphate ester ranges from about 5 to about 10 wt %, based on the total weight of the alkylated triaryl phosphate ester.

The present invention also relates to a process for making alkylated triaryl phosphate esters comprising:

a) reacting an alkylated phenol comprising less than about 1 mole % phenol and up to about 75 mole % dialkyl phenol, both based on the total moles of reactive alkylated phenolics in the alklyated phenol, with $POCl_3$ in the presence of a first catalyst under first reaction conditions including temperatures ranging from about 80° C. to about 210° C. thereby producing a first reaction product comprising greater than about 75 mole % monoalkylated phenyl-dichloro phosphates, based on the total moles of the first reaction product; and b) reacting the first reaction product with an alcohol selected from aryl alcohols, alkyl alcohols, alkylated aryl alcohols, and mixtures thereof in the presence of a second catalyst under second reaction conditions including temperatures ranging from about 90° C. to about 260° C. thereby producing an alkylated triaryl phosphate ester.

The present invention also relates to a process for making alkylated triaryl phosphate esters comprising:

a) reacting an alkylated phenol comprising less than about 1% phenol and up to about 75% dialkyl phenol, both based on the total weight of the alkylated phenol, with a molar excess of $POCl_3$ in the presence of a first catalyst under first reaction conditions including temperatures ranging from about 80° C. to about 210° C. thereby producing a first reaction product comprising greater than about 50 mole %, based on the total moles of the first reaction product, monoalkylated phenyldichloro phosphates and excess $POCl_3$;

b) removing at least a portion of the excess $POCl_3$ from the first reaction product to produce an intermediate product, wherein said intermediate reaction product contains less than 15 mole % phosphorus, based on the total moles of the intermediate reaction product, in the form of $POCl_3$ remains; and c) reacting the first reaction product with an alcohol selected from aryl alcohols, alkyl alcohols, alkylated aryl alcohols, and mixtures thereof in the presence of a second catalyst under second reaction conditions including temperatures ranging from about 90° C. to about 260° C. thereby producing an alkylated triaryl phosphate ester.

DETAILED DESCRIPTION OF THE INVENTION

As used herein, "IP's" is meant to refer to isopropylatedphenols; "OIP" is meant to refer to ortho-isopropylphenol; "MIP" is meant to refer to meta-isopropylphenol; "PIP" is meant to refer to para-isopropylphenol; "TPP" is meant to refer to triphenyl phosphate; "2,6-DIP" is meant to refer to 2,6-diisopropylphenol; "2,4-DIP" is meant to refer to 2,4-diisopropylphenol; "2,4,6-TIP" is meant to refer to 2,4,6-triisoproplylphenol; "2-IPP" is meant to refer to 2-isopropylphenyl diphenyl phosphate; "3-IPP" is meant to refer to 3-isopropylphenyl diphenyl phosphate; "4-IPP" is meant to refer to 4-isopropylphenyl diphenyl phosphate; "2,4-DDP" is meant to refer to 2,4-diisopropylphenyl diphenyl phosphate; "IPP's" is meant to refer to isopropylated triphenyl phosphates; "DTPP" is meant to refer to diisopropylated triphenyl phosphate; and "TTPP" is meant to refer to triisopropylated triphenyl phosphate.

Alkylated Triaryl Phosphate Esters

In one embodiment, the present invention relates to alkylated triaryl phosphate esters. The alkylated triaryl phosphate esters of the present invention are characterized as containing less than about 1 wt % TPP, based on the total weight of the alkylated triaryl phosphate ester, in some embodiments less than about 0.75 wt % TPP, on the same basis, and in other embodiments, less than about 0.5 wt % TPP, on the same basis.

Despite the low concentrations of TPP, the alkylated triaryl phosphate esters of the present invention still contain a high amount of phosphorus. Typically the alkylated triaryl phosphate esters of the present invention contain from about 5 to about 10 wt % organic phosphorous, based on the total weight of the alkylated triaryl phosphate ester. Preferably the organic phosphorus content ranges from about 7 to about 9 wt %, on the same basis, and in more preferred embodiments the organic phosphorous content ranges from about 7.5 to about 8.5 wt %, most preferably in the range of from about 8.0 to about 8.4%, on the same basis.

In some embodiment, the alkylated triaryl phosphate esters of the present invention are further characterized as containing greater than about 20 wt % monalkylphenyl diphenyl phosphates, based on the total weight of the alkylated triaryl phosphate ester. Preferably, the alkylated triaryl phosphate esters contain greater than about 75 wt %, on the same basis, of monalkylphenyl diphenyl phosphates, more preferably greater than about 90 wt %, on the same basis.

The alkylated triaryl phosphate esters of the present invention can further be characterized as containing less than about 80 wt % di-(alkylphenyl)phenyl phosphates, based on the total weight of the alkylated triaryl phosphate ester. Preferably the alkylated triaryl phosphate esters of the present invention contain less than about 25 wt %, more preferably less than about 10 wt %, di-(alkylphenyl)phenyl phosphates, on the same basis.

The alkylated triaryl phosphate esters of the present invention can also be further characterized as containing less than about 50 wt %, based on the total weight of the alkylated triaryl phosphate ester, dialkylphenyl diphenyl phosphates. However, in preferred embodiments, the alkylated triaryl phosphate esters of the present invention contain less than about 25 wt %, more preferably less than about 10 wt %, dialkylphenyl diphenyl phosphates, on the same basis. In a most preferred embodiment, the alkylated triaryl phosphate esters of the present invention contain less than about 1 wt %, based on the total weight of the alkylated triaryl phosphate ester, dialkylphenyl diphenyl phosphates. The inventors hereof have unexpectedly discovered that, in some embodiments, the removal of unreacted alkylated phenols during the production of the alkylated triaryl phosphate esters of the present invention is more efficient for alkylated triaryl phosphate esters having these concentrations of dialkylphenyl diphenyl phosphates.

The amount of trialkylphenyl phosphates present in the alkylated triaryl phosphate esters of the present invention is generally less than about 20 wt %, based on the total weight of the alkylated triaryl phosphate ester. However, in preferred embodiments, the alkylated phenyl phosphates of the present invention can contain less than about 2 wt %, on the same basis, of trialkylphenyl phosphates. In some most preferred embodiments the level of trialkylphenyl phosphates is less than 0.5 wt %, on the same basis. The alkylated phenyl phosphates according to the present invention also comprise less than about 20 wt %, based on the total weight of the alkylated triaryl phosphate ester, alkylphenyl dialkylphenyl phenyl phosphates. In most preferred embodiments the alkylated triaryl phosphate esters of the present invention contain less than 0.05 wt %, based on the total weight of the alkylated triaryl phosphate ester, of the alkylphenyl dialkylphenyl phenyl phosphates.

Exemplary alkylated triaryl phosphate esters of the present invention are those a) those that comprise: in the range of from about 90 to about 92 wt. % IPP, in the range of from about 0.5 to about 0.75 wt. % TPP, in the range of from about 1 to about 3 wt. % DTPP, in the range of from about 0.05 to about 0.15 wt. % TTPP, and in the range of from about 0.5 to about 0.75 wt. % 2,4-DDP; b) in the range of from about 94 to about 96 wt. %/IPP, in the range of from about 3.5 to about 5.5 wt. % DTPP, and in the range of from about 0.1 to about 0.3 wt % TTPP; and c) in the range of from about 71 to about 73 wt. % IPP, in the range of from about 0.05 to about 0.15 wt. % TPP, in the range of from about 26 to about 28 wt. % DTPP, and in the range of from about 0.5 to about 0.7 wt. % TTPP.

Monoalkylphenyl diphenyl phosphates, di-(alkylphenyl) phenyl phosphates, dialkylphenyl diphenyl phosphates, trialkylphenyl phosphates, and alkylphenyl dialkylphenyl phenyl phosphates, present in the alkylated triaryl phosphate esters of the present invention are those wherein the alkyl moieties are selected from methyl, ethyl, propyl, isopropyl, butyl, isobutyl, tertiary-butyl, amyl, isoamyl, tertiary-amyl groups, and cyclohexyl alkyl moieties. Preferably, the alkyl moieties of at least one of, preferably at least two of, more preferably all of, the monoalkylphenyl diphenyl phosphates, di-(alkylphenyl)phenyl phosphates, dialkylphenyl diphenyl phosphates, trialkylphenyl phosphates, and alkylphenyl dialkylphenyl phenyl phosphates, present in the alkylated triaryl phosphate esters are isopropyl moieties. Thus, for example, in a most preferred embodiment, the alkylated triaryl phosphate esters according to the present invention are isopropylphenyl diphenyl phosphate esters. Of the total isopropylphenyl diphenyl phosphate esters, 0.1 to 99.9 wt % is 2-isopropylphenyl phosphate (2-IPP), 0.1 to 99.9 wt % is 3-isopropylphenyl phosphate (3-IPP), 0.1 to 99.9 wt % is 4-isopropylphenyl phosphate (4-IPP), all based on the total weight of the alkylated triaryl phosphate ester. In the most preferred embodiments 66 to 100 wt % of the isopropylphenyl phenyl phosphate present in the alkylated triaryl phosphate esters according to the present invention is 2-isopropylphenyl phosphate (2-IPP), 0.1 to 4-wt % is 3-isopropylphenyl phosphate (3-IPP), 0.1 to 40 wt % is 4-isopropylphenyl phosphate (4-IPP). It should be noted that although specific ranges of isopropylphenyl phenyl phosphate have been discussed above, it is within the scope of the present invention to produce an alkylated triaryl phosphate ester having any possible relative ratio of 2-IPP, 3-IPP and 4-IPP. However, in a most preferred embodiment, the alkylated triaryl phosphate esters according to the present invention are isopropylphenyl diphenyl phosphate esters wherein in the range of about 63 to about 68% of the isopropylphenyl diphenyl phosphate ester is 2-IPP, in the range of from about 0.5 to about 2.5% is 3-IPP and in the range of from about 30.5 to about 36.5% is 4-IPP. In an exemplary embodiment of the present invention, the alkylated triaryl phosphate esters according to the present invention are isopropylphenyl diphenyl phosphate esters wherein about 66% of the isopropylphenyl diphenyl phosphate ester is 2-IPP, about 1% is 3-IPP and about 33% is 4-IPP. The alkylated triaryl phosphate esters of the present invention can suitably be formed by a process comprising reacting an alkylated phenol with $POCl_3$ in the presence of a first catalyst, thus forming a first reaction product. The first reaction product is then reacted with an alcohol selected from aryl alcohols, alkyl alcohols, alkylated aryl alcohols, and mixtures thereof in the presence of a second catalyst under second reaction conditions including temperatures ranging from about 90° C. to about 260° C. thereby producing an alkylated triaryl phosphate ester according to the present invention. It should be noted that the reaction that produces the first reaction product is sometimes referred to as the first reaction herein, and the reaction of the first reaction product with the alcohol is sometimes referred to herein as the second reaction.

First Reaction—Alkylated Phenol

Alkylated phenols suitable for use in the first reaction include those wherein the alkyl group is selected from methyl, ethyl, n-propyl, isopropyl, isobutyl, tertiary-butyl, amyl, isoamyl, tertiary-amyl alkyl moieties, and cyclohexyl, preferably isopropyl moieties.

Preferably, the alkylated phenol that is reacted with the $POCl_3$ in the presence of the first catalyst contains less than 1 mole % phenol and less than 25 mole % dialkyl phenol, both based on the total moles of reactive alkylated phenols (as described below) in the alklyated phenol. In a more preferred embodiment, the alkylated phenol contains less than 0.5 mole % phenol and less than 15 mole % dialkyl phenol, both based on the total moles of reactive alkylated phenols in the alklyated phenol. In a most preferred embodiment, the alkylated phenol contains less than 0.5 mole % phenol and less than 5 mole % 2,4-diisopropylphenol, both based on the total moles of reactive alkylated phenolics in the alklyated phenol. In preferred embodiments, the dialkyl phenol of the alkylated phenol is 2,4-disiopropylphenol.

In an even more preferred embodiment, the alkylated phenol stream comprises essentially OIP, MIP, and PIP constituents. In this embodiment, it is preferred that the alkylated phenol stream comprise in the range of from about 64 to about 68 wt. % OIP, in the range of from about 0.5 to about 2.5 wt. % MIP, and in the range of from about 31 to about 35 wt. % PIP, all based on the total weight of the alkylated phenol.

"Total moles of reactive alkylated phenols" and "Reactive alkylated phenol" as used herein is meant to refer to the total moles of alkylated phenols that are part of the reaction between the alkylated phenol and the $POCl_3$. This unit of measure is used herein because unreactive alklyated phenols are also present in the alkylated phenol. For example, 2,6-DIP and 2,4,6-TIP are common impurities in an IP's stream but are for all intents and purposes unreactive. For example, see Table 1 below, which describes one example of an alkylated phenol suitable for use herein:

TABLE 1

| ISOPROPYLATED PHENOL STREAM | | | | |
|---|---|---|---|---|
| Component | FW | GC wt % | Mole/100 g | Reactive Moles/100 g |
| Phenol | 94.11 | 0.35 | 0.0037 | 0.0037 |
| OIP | 136.19 | 59.48 | 0.4367 | 0.4367 |
| PIP | 136.19 | 29.76 | 0.2185 | 0.2185 |
| 2,6-DIP | 178.27 | 4.25 | 0.0238 | Inert |
| 2,4-DIP | 178.27 | 5.83 | 0.0327 | 0.0327 |
| 2,4,6-TIP | 220.35 | 0.32 | 0.0015 | Inert |
| Average FW | | | 139.76 | *134.83 |

In Table 1, the amounts described herein as based on the total moles of reactive alkylated phenols would thus be based on 134.83 moles.

First Reaction—$POCl_3$

The amount of $POCl_3$ used herein can be a molar equivalency, in some embodiments a molar excess, and in other embodiments, less than a molar equivalency. By a molar equivalency of $POCl_3$, it is meant that a molar ratio of about 1 moles of $POCl_3$ to about 1 mole of reactive alkylated phenol. By a molar excess of $POCl_3$, it is meant that a molar ratio of greater than 1 moles of $POCl_3$ to 1 mole of reactive alkylated phenol. Preferably a molar excess is in the range of from about 1.0 to about 5.0 moles of $POCl_3$ to about 1 mole of reactive alkylated phenol, and more preferably in the range of from about 1.15 to about 2.5 moles of $POCl_3$ to about 1 mole of reactive alkylated phenol are used in the practice of this embodiment of the present invention.

By less than a molar equivalency of $POCl_3$, it is meant a molar ratio of less than 1 mole of $POCl_3$ to 1 mole of reactive alkylated phenol. For example, in one embodiment, which would produce a first reaction product having significantly higher DTTP and TTPP, a molar excess of alklyated phenol can be used, i.e. less than a molar equivalency of $POCl_3$. In this embodiment, it is preferred to use greater than in the range of from about 1 to about 2, preferably in the range of from 1.1 to about 1.2, moles of reactive alkylated phenol per mole of $POCl_3$.

Reactive alkylated phenol is defined above.

First Catalyst

Catalysts suitable for use as the first catalyst herein can be selected from tertiary amines such as trialkyl amines, dialkylaryl amines, and heterocyclic tertiary amines such as 1,4 Diazabicyclo[2,2,2]octane (DABCO); aromatic amines such as pyridine and substituted pyridines with N,N-dimethylaminopyridine being preferred from this group; pyrimidines and its derivatives; pyrazine and its derivatives; pyroles and its derivatives; imidizoles, its derivatives and their corresponding mineral and organic acid salts with N-methylimidazole, imidiazole and its derivatives being preferred from this group; quaternary ammonium salts; quaternary phosphonium salts; tetrakis dialkylamino phosphonium salts having the general formula $P(NRR')_4{}^+X^-$ especially tetrakis diethylamino phosphonium Bromide having the formula $P(NEt_2)_4{}^+Br^-$, alkali metal halide catalysts; and alkali earth metal halides, oxides, sulfates, sulfonates, hydroxides, and phosphates. It should be noted that any alkali metal halide and salts, e.g. ammonium, phosphonium, etc., as described above, can be used as long as the salt/halide has appreciable solubility to initiate the reaction with $POCl_3$ such that co-produced hydrogen chloride ultimately converts the metal catalyst salt to the metal chloride salt. Non-limiting examples of alkali metal and alkali earth metal catalysts include $AlCl_3$, $MgCl_2$, $CaCl_2$, NaCl, KCl, $FeCl_3$, LiCl, $TiCl_4$, $SbCl_4$, AgCl and $BaCl_2$. Non-limiting examples of suitable quaternary ammonium salts include tetrabutylammonium halide, tetra alkyl or mixed alkyl ammonium mineral or organic acid salt. Non-limiting examples of suitable quaternary phosphonium salts include any tetra alkyl or tetraaryl phosphonium salt. Preferably the first catalyst is selected from quaternary ammonium salts, quaternary phosphonium salts, tetrabutylammonium chloride, $MgCl_2$, and pyridine. In one preferred embodiment the first catalyst is tetrabutylammonium chloride. In yet another preferred embodiment the first catalyst is $MgCl_2$. In a particularly preferred embodiment, the first catalyst is pyridine.

First Reaction Conditions

The $POCl_3$ and alkylated phenol are reacted under first reaction conditions that include temperatures ranging from about 75° C. to about 210° C. Preferably, first reaction conditions include temperatures ranging from about 80° C. to about 150° C., more preferably temperatures ranging from about 90° C. to about 140° C. The reactants and first catalyst can be combined, contacted, etc. in any order. However, it is preferred that the alkylated phenol reactant be added to the $POCl_3$ reactant. It has been found that an alkylated phenol phosphate with superior viscosity, i.e. less viscous, can be produced by combining the reactants and catalyst in this order. In a more preferred embodiment, the alkylated phenol is added to a reaction vessel containing both the $POCl_3$ reactant and first catalyst.

It should be noted that the reaction between the alkylated phenol and $POCl_3$ produces HCl gas, which can cause undesirable cleavage and/or transesterification reactions. Thus, in preferred embodiments, first reaction conditions also include venting of HCl gas. This venting can be conducted by any means known to be effective at venting HCl gas from a reaction vessel. However, in preferred embodiments, the venting is accomplished by conducting the reaction under first reaction conditions that include sub-atmospheric pressures, i.e. under a vacuum. The amount of vacuum used is readily selected by one having ordinary skill in the art taking into consideration that too much vacuum would cause the reaction temperature to fall outside of the ranges described above, thus slowing the reaction rate. Further, while vacuum pressures are preferred, the reaction can be conducted at atmospheric pressures up to about 5 psig and still produce a desirable product, albeit at a slightly reduced rate. A pressure significantly above 5 psig would slow the reaction rate somewhat more and potentially lead to the undesirable cleavage and/or transesterification reactions.

In preferred embodiments, first reaction conditions further include the substantial absence of oxygen.

First Reaction—Optional Diluent

In some embodiments, a diluent can be added along with the $POCl_3$, first catalyst, and alkylated phenol. Diluents suitable for use herein are those that i) do not react substantially with the reagents, products and co-products, including HCl, utilized or generated during the first and/or second reactions; and ii) do not substantially reduce the catalytic activity of the first and/or second catalyst. In preferred embodiments, diluents suitable for use herein can be further characterized as those that iii) do not lower the reaction temperature such that the reaction rate slows significantly to the point of not being commercially feasible, i.e. below the ranges disclosed herein. It should be noted that the diluent can be added as a complex with the first catalyst. Non-limiting examples of suitable diluents include a) hydrocarbon solvents, such as heptane, petroleum ethers, methylcyclohexane and boiling point heptane; b) aromatic hydrocarbons such as toluene, xylene(s) and ethyl benzene; c) halo hydrocarbons and halo aromatic hydrocarbons such as chlorobenzene, dibromomethane, dibromoethane, and all isomers of trichloroethylene; d) ether solvents such as, tetrahydrofuran or 1,4-dioxane. Preferably, if an ether diluent is used, the diluent is 1,4-dioxane. In a most preferred embodiment, the diluent is toluene.

First Reaction Product

The reaction of the $POCl_3$ and alkylated phenol produces a first reaction product comprising greater than about 50 mole % monoalkylatedphenyl dichloro phosphates, based on the total moles of the first reaction product excluding unreacted $POCl_3$ and any added diluent.

In some embodiments, the first reaction product can comprise in the range of from about 70 to about 99.9 mole % monoalkylatedphenyl dichloro phosphates, on the same basis, and in the range of from about 0.1 mole % to about 30 mole % bis-(monoalkylated)phenyl-chloro phosphates, on the same basis.

By excess $POCl_3$ it is meant any $POCl_3$ that did not react with the alkylated phenol, i.e. unreacted $POCl_3$ it. Typically, the first reaction product comprises in the range of from about 5 to about 80 mole % unreacted $POCl_3$, based on the total phosphorus in the first reaction product, as determined by some suitable method, preferably quantitative P-31 NMR. The amount of unreacted $POCl_3$ in the first reaction product is obviously dependent on the amount of $POCl_3$ used in the first reaction stage. For example, if less than a molar equivalency of $POCl_3$ is used, then the first reaction product can contain substantially no excess $POCl_3$, depending on the efficiency of the reaction between the alkylated phenol and $POCl_3$; however, if a molar excess of $POCl_3$ is used, then the amount of excess $POCl_3$ will depend on the efficiency of the reaction and on the amount of $POCl_3$ used. In the practice of the present invention, if less than a molar equivalency, or up to about a 15% molar excess of $POCl_3$, is used to produce the first reaction product, then the first reaction product can be, and in some embodiments is, directly reacted with an alcohol without removal of unreacted $POCl_3$.

Optional $POCl_3$ Removal

If excess $POCl_3$ is used in producing the first reaction product, then it is preferred that at least a portion of the excess $POCl_3$ be removed from the first reaction product, thereby producing an intermediate reaction product. In preferred embodiments, the amount of excess $POCl_3$ removed from the first reaction product is that amount necessary to produce an intermediate product containing less than about 15 mole %, preferably less than about 10 mole %, more preferably less than about 5 mole %, most preferably less than about 1 mole %, $POCl_3$, all based on the total phosphorus in the first reaction product. In a particularly preferred embodiment, substantially all unreacted $POCl_3$ is removed from the first reaction product, which in some embodiments can produce an intermediate reaction product that contains substantially no unreacted alkylated phenol. However, it should be noted that if the intermediate reaction product is reacted with phenol, the amount of unreacted $POCl_3$ removed from the first reaction product must be that amount necessary to produce an intermediate product containing less than about 1.2 mole %, preferably less than about 1 mole % of total organic phosphorus.

The method by which the $POCl_3$ is removed from the first reaction product to produce the intermediate product is not critical to the present invention, and non-limiting examples of suitable removal techniques include vacuum distillation, flashing, stripping, vacuum stripping, and the like. In preferred embodiments, $POCl_3$ is removed by vacuum stripping. Vacuum stripping can suitably be carried out by heating the first reaction product to within the range of about 115° C. to about 170° C., under constant agitation and vacuum in the range of from about 700 mmHg to about 0.001 mmHg. It is within the scope of the present invention that a nitrogen purge accompany the vacuum stripping. It is also within the scope of the present invention to add an inert "chaser" solvent at the end of the vacuum stripping to reduce the $POCl_3$ in the intermediate reaction product to less than 1 mole %, based on the intermediate reaction product. If a chaser solvent is used, it is preferred to use toluene, methylcyclohexane, boiling-point heptanes or n-heptane.

It should be noted that, while not necessary, in some embodiments, the optional $POCl_3$ removal is accompanied by the removal of a portion of any diluent added during the first reaction. In this embodiment, conditions can be adjusted to within the above ranges and means selected from those described above to provide for more efficient removal of both the $POCl_3$ and diluent.

Second Reaction

In the practice of the present invention, the first reaction product or intermediate reaction product is reacted with an alcohol selected from aryl alcohols including phenol, alkyl alcohols, alkylated aryl alcohols, and mixtures thereof in the presence of a second catalyst or processed to remove at least a portion of excess $POCl_3$.

In an alternative embodiment, the first reaction product or intermediate product can be reacted sequentially with more than one alcohol selected from aryl alcohols including phenol, alkyl alcohols, alkylated aryl alcohols, and mixtures thereof. In this embodiment, it is preferred that the first reaction product or intermediate product be reacted with a first alcohol, and when the first alcohol has been consumed, as determined by a suitable method such as $P^{31}$ NMR, a second alcohol, preferably different from the first alcohol, be added.

More preferably, in this embodiment, the first alcohol is divided into a first and second portion. The first reaction product or intermediate reaction product is reacted with the first portion of the first alcohol until substantially all of the first portion of the first alcohol is consumed, as determined by a suitable method such as $P^{31}$ NMR. After substantially all of the first portion of the first alcohol has been consumed, the second portion of the first alcohol is added, and the reaction allowed to continue until substantially all of the second portion of the first alcohol has been consumed, as determined by a suitable method such as $P^{31}$ NMR, thus producing a first intermediate reaction product comprising at least aryl dichlorophosphate and chloro diarylphosphate.

The first intermediate reaction product, which is richer, i.e. has a higher concentration, in chloro diarylphosphates then the first reaction product, is then reacted with an effective amount of the second alcohol. By an effective amount of the second alcohol, it is meant that amount of the second alcohol that is effective at converting substantially all of the aryl dichlorophosphate and chloro diarylphosphate to alkylated triaryl phosphate esters according to the present invention.

In this embodiment, the first and second alcohol can be independently selected from aryl alcohols including phenol, alkyl alcohols, alkylated aryl alcohols, and mixtures thereof.

Non-limiting examples of suitable alkylated aryl alcohols are those wherein the alkyl group contains from about 1 to about 5 carbon atoms such as methyl. Non-limiting examples of suitable alkyl alcohols are those wherein the alkyl group contains from about 1 to about 20 carbon atoms such as n-decanol. Preferably the alcohol is selected from phenol, decanol, dodecanol or mixtures thereof and in a most preferred embodiment, the alcohol is phenol.

Second Catalyst

Catalysts suitable for use as the second catalyst herein can be selected from quaternary ammonium salts, quaternary phosphonium salts, $MgCl_2$, $CaCl_2$, $AlCl_3$, $KCl$, $FeCl_3$, $LiCl$, and $BaCl_2$. Non-limiting examples of suitable quaternary ammonium salts and quaternary phosphonium salts include are those listed above in relation to the first catalyst. Preferably the second catalyst is selected from $MgCl_2$, $CaCl_2$, $AlCl_3$, $KCl$, $FeCl_3$, $LiCl$, and $BaCl_2$. More preferably the second catalyst is $MgCl_2$.

Second Reaction Conditions

The first reaction product or intermediate reaction product and alcohol are reacted in the presence of the second catalyst under second reaction conditions including temperatures ranging from about 75° C. to about 260° C. Preferably, second reaction conditions include temperatures ranging from about 100° C. to about 180° C., most preferred from about 140° C. to about 150° C. The first reaction product or intermediate reaction product, alcohol, and second catalyst can be combined, contacted, etc., in any order. For example, the first reaction product or intermediate reaction product, alcohol, and second catalyst can be co-fed to a reaction vessel, the first reaction product or intermediate reaction product can be added to a reaction vessel containing the alcohol and second catalyst, etc. However, it is preferred that the alcohol, preferably in the molten or liquid state, be added to the first reaction product reactant or intermediate reaction product to which the second catalyst has already been introduced. The inventors have unexpectedly discovered that combining, contacting, etc. the first reaction product or intermediate reaction product, second catalyst and alcohol in this manner provides for an alkylated phenol phosphate having TPP concentrations lower than those formed when the reactants are not added in this manner. In this embodiment, the catalyst is preferably present with the alcohol, but it can be co-fed or fed after the intermediate product.

In preferred embodiments, second reaction conditions further include the substantial absence of oxygen.

The reaction of the first reaction product or intermediate reaction product and alcohol produces an alkylated triaryl phosphate ester according to the present invention, as described above.

Optional Processing of Alkylated Triaryl Phosphate Ester

In some embodiments, it may be desirable to further refine the alkylated triaryl phosphate ester produced from the present process, for example to remove any excess alcohol that may be present in the alkylated triaryl phosphate ester. Further processing can also include adding an additional amount of alcohol such as monoisopropylated phenols, diisopropylated phenols, phenol, and mixtures thereof and/or second catalyst to the alkylated triaryl phosphate ester. The alcohol-rich alkylated triaryl phosphate ester product comprising excess alcohol can then be recovered, and at least a portion, preferably substantially all, of the excess alcohol removed by, for example, phase separation and/or stripping and/or distillation. In preferred embodiments, steam stripping is used.

The alkylated triaryl phosphate ester may also be washed one or more times with an acid, a base, or water. In this embodiment, the alkylated triaryl phosphate ester can first be washed with an acid and/or base, preferably a base, and then washed with water. In this embodiment, it is preferred to wash the alkylated triaryl phosphate ester with a base such as NaOH, preferably a diluted base comprising in the range of about 1 to about 5 wt. %, based on the diluted base, NaOH, in the range of about 1 to about 4 times, followed by washing with water until the pH of the water recovered from the washing is in the range of from about 7 to about 9.

In another embodiment, the alkylated triaryl phosphate ester can also be processed in a wipe film evaporator, a distillation column, or other similar separation device, in conjunction with the above further refinement processes or as a stand-alone refinement.

Use of Alkylated Triaryl Phosphate Esters as Flame Retardant

The alkylated triaryl phosphate esters of the present invention are suitable for use as a flame retardant in many applications. In particular, the alkylated triaryl phosphate esters of the present invention are especially well suited for use in polyurethane foams, polymer resins, and polyester resins.

In one embodiment, the present invention relates to a flame retardant polyvinyl chloride resin formulation comprising at least one, in some embodiments only one, polyvinyl chloride resin and a flame retarding amount of at least one, in some embodiments only one, alkylated triaryl phosphate ester, as described herein. By a flame retarding amount of alkylated triaryl phosphate ester, it is meant in the range of from about 2 to about 150 parts per hundred resin ("phr") of the at least one alkylated triaryl phosphate ester, based on the total weight of the flame retardant polyvinyl chloride resin formulation. In preferred embodiments, a flame retarding amount of alkylated triaryl phosphate ester is to be considered in the range of from about 5 to about 70 phr, more preferably in the range of from about 12 to about 45 phr, of the at least one alkylated triaryl phosphate ester, on the same basis.

Resins suitable for use in this embodiment of the present invention include those comprising a polymer comprised of one or more polymerized monomers having a polymerizable olefinic double bond in the molecule. There are three groups of such polymers, namely (i) one or more vinylaromatic homopolymers or copolymers, preferably high-impact polystyrene, (ii) one or more acyclic olefinic hydrocarbon homopolymers or copolymers, such as polyethylene, polypropylene, and copolymers of ethylene or propylene with at least one higher olefin and with or without a diene monomer, and (iii) one or more copolymers of at least one vinylaromatic monomer and at least one non-vinylaromatic monomer containing a functional group, such as acrylonitrile, an acrylate monomer, or a methacrylate monomer with or without a diene monomer. Examples of group (ii) include ABS, MBS, SAN, and ASA. Of the above three groups of polymers, preferred are vinylaromatic polymers.

Vinylaromatic polymers that can be flame retarded in the practice of this invention can be homopolymers, copolymers or block polymers and such polymers can be formed from such vinylaromatic monomers as styrene, ring-substituted styrenes in which the substituents are one or more $C_{1-6}$ alkyl groups, alpha-methylstyrene, ring-substituted alpha-methylstyrenes in which the substituents are one or more $C_{1-6}$ alkyl groups, vinylnaphthalene, and similar polymerizable styrenic monomers, i.e., styrenic compounds capable of being polymerized, e.g., by means of peroxide or like catalysts, into thermoplastic resins. Homopolymers and copolymers of simple styrenic monomers (e.g., styrene, p-methyl-styrene, 2,4-dimethylstyrene, alpha-methyl-styrene, p-chloro-styrene, etc.) are preferred from the standpoints of cost and availability. The vinylaromatic polymers that are flame retarded pursuant to this invention can be homopolymers or copolymers can be produced by free-radical polymerization, cationically-initiated polymerization, or anionically-initiated polymerization. In addition, the vinylaromatic polymers that are flame retarded in the practice of this invention can be foamable, expanded, or foamed vinylaromatic polymer compositions. The vinylaromatic polymers can have various structural configurations. For example they can be isotactic polymers, syndiotactic polymers, or mixtures of isotactic and syndiotactic polymers. In addition the vinylaromatic polymers can be in the form of blends or alloys with other thermoplastic polymers, such as polyphenylene ether-styrenic polymer blends and polycarbonate-styrenic polymer blends. The vinylaromatic polymers can be impact-modified or rubber-modified polymers. In some embodiments, the resin is a polyvinyl chloride resin.

In these embodiments, the flame retardant resin formulation can also include conventional additives such as, for example, process aids, acid scavengers, dyes, pigments, fillers, stabilizers, antioxidants, antistatic agents, reinforcing agents, blowing agents, nucleating agents, plasticizers, and the like. The amount of these additives used in the flame retardant polyvinyl chloride resin formulation is conventional, and one having ordinary skill in the art can readily select the amount and specific additive depending on the desired characteristics of the flame retardant polyvinyl chloride resin formulation.

The alkylated triaryl phosphate esters of the present invention are suitable for use as a flame retardant in polyurethane/polyisocyanurate foams and polyurethane/polyisocyanurate foam formulations. Thus, in some embodiments, the present invention relates to polyurethane/polyisocyanurate foams, polyurethane/polyisocyanurate foam formulations, and processes for forming flame retarded polyurethane/polyisocyanurate foam formulations, both rigid and flexible, all containing a flame retarding amount of at least one, in some embodiments only one, alkylated triaryl phosphate ester, as described herein. In some embodiments, the present invention relates to polyurethane foams, polyurethane foam formulations, and processes for forming flame retarded polyurethane foam formulations, both rigid and flexible, in some embodiments flexible all containing a flame retarding amount of at least one, in some embodiments only one, alkylated triaryl phosphate ester, as described herein. By a flame retarding amount of alkylated triaryl phosphate ester, it is meant in the range of from about 5 to about 75 wt. % of the at least one alkylated triaryl phosphate ester, based on the total weight of the polyurethane/polyisocyanurate foams or polyurethane/polyisocyanurate foam formulations. In preferred embodiments, a flame retarding amount of alkylated triaryl phosphate ester is to be considered in the range of from about 5 to about 70 wt. %.

The polyurethanes and polyisocyanurates, the foams thereof, and methods of preparing such polymers are very well known in the art and are reported in the literature. See, for example, Encyclopedia of Polymer Science and Technology, vol. 11, pgs. 506 563 (1969 Wiley & Sons) and vol. 15, pp. 445 479 (1971 Wiley & Sons), U.S. Pat. Nos. 3,974,109; 4,209,609; 4,405,725; 4,468,481; 4,468,482; 5,102,923; 5,164,417; 7,045,564; and 7,153,901; and U.S. patent application Ser. No. 11/569,210, which are all incorporated herein by reference in their entirety. For example, flexible polyurethane foams are typically prepared by chemical reaction between two liquids, isocyanates and polyols. The polyols are polyether or polyester polyols. The reaction readily occurs at room temperature in the presence of a blowing agent such as water, a volatile hydrocarbon, halocarbon, or halohydrocarbon, or mixtures of two or more such materials. Catalysts used in effecting the reaction include amine catalysts, tin-based catalysts, bismuth-based catalysts or other organometallic catalysts, and the like. Surfactants such as substituted silicone compounds are often used in order to maintain homogeneity of the cells in the polymerization system. Hindered phenolic antioxidants, e.g., 2,6-di-tert-butyl-para-cresol and methylenebis(2,6-di-tert-butylphenol), can be used to further assist in stabilization against oxidative degradation.

In some embodiments, the present invention also relates to a polyurethane/polyisocyanurate foam formulation comprising a flame retarding amount of at least one, in some embodiments only one, alkylated triaryl phosphate ester, as described herein; at least one, in some embodiments only one, isocyanate or polyol; and at least one, in some embodiments only one, blowing agent, and polyurethane/polyisocyanurate foams, both rigid and flexible, formed therefrom. Blowing agents suitable for use herein include water, a volatile hydrocarbon, halocarbon, or halohydrocarbon, or mixtures of two or more such materials.

In addition to these components the polyurethane/polyisocyanurate foams and foam formulations can contain any other component known in the art and used in the formation for flexible and rigid polyurethane/polyisocyanurate foams, and these other components used in forming polyurethane polymerization formulations or recipes are well known to those of ordinary skill in the art. For example, the polyurethane/polyisocyanurate foam formulations can contain surfactants, antioxidants, diluents such as low viscosity liquid $C_{1-4}$ halocarbon and/or halohydrocarbon diluents in which the halogen content is 1-4 bromine and/or chlorine atoms can also be included in the compositions of this invention. Non-limiting examples of such diluents include bromoehloromethane, methylene chloride, ethylene dichloride, ethylene dibromide, isopropyl chloride, n-butyl bromide, sec-butyl bromide, n-butyl chloride, sec-butyl chloride, chloroform, perchloroethylene, methyl chloroform, and carbon tetrachloride.

It should be noted that these and other ingredients that can be used in the polyurethane/polyisocyanurate foam formulations of the present invention, and the proportions and manner in which they are used are reported in the literature. See for example: Herrington and Hock, Flexible *Polyurethane* Foams, The Dow Chemical Company, 1991, 9.25 9.27 or Roegler, M "Slabstock Foams"; in *Polyurethane* Handbook; Oertel, G., Ed.; Hanser Munich, 1985, 176 177 or Woods, G. Flexible *Polyurethane* Foams, Chemistry and Technology; Applied Science Publishers, London, 1982, 257 260, which is hereby incorporated by reference in its entirety, and U.S. patent application Ser. No. 11/569,210, which has already been incorporated herein by reference.

The above description is directed to several embodiments of the present invention. Those skilled in the art will recognize that other means, which are equally effective, could be devised for carrying out the spirit of this invention. It should also be noted that preferred embodiments of the present invention contemplate that all ranges discussed herein include ranges from any lower amount to any higher amount. For example, when discussing the second reaction conditions, these ranges can include temperatures in the range of from about 75° C. to about 100° C., 90° C. to about 180° C., 100° C. to about 260° C., 150° C. to about 180° C., etc.

The following examples will illustrate the present invention, but are not meant to be limiting in any manner.

EXAMPLES

In the following Examples, the notation "Wt % in Crude" indicates the amount of each component in the ester product recovered from the reactor, and is thus based on the total weight of the product recovered from the reactor. "Normalized wt %" indicates the amount of each component calculated by dividing the "Wt % in Crude" values by the "Normalization Factor", thus indicating the amount of each component in relation to the alkylated triaryl phosphate ester.

Example 1 (Comparative)

A reaction flask was purged with nitrogen. 15.3 g (0.1 mole) of phosphorous oxychloride ("$POCl_3$") followed by 13.6 g (0.1 mole) of ortho-isopropylphenol ("OIP"). The mixture was heated to about 110° C. for 10 hours under agitation. The content of the flask were analyzed via $^1$H-NMR and it was discovered that greater than 50 mol. % of the OIP was unreacted. The content of the flask were also analyzed via $^{31}$P-NMR, and the molar ratio of 2-isopropylphenyl dichlorophosphate to bis-(2-isopropylphenyl) chlorophosphate bis to tris-(2-isopropylphenyl) phosphate was found to be 40.8:22.6:5.0.

Example 2 (Comparative)

A reaction flask was purged with nitrogen. 15.3 g (0.1 mole) of phosphorous oxychloride ("$POCl_3$") followed by 13.6 g (0.1 mole) of ortho-isopropylphenol ("OIP") was then added to the flask over a 30 minute period. The mixture was heated to 195° C. for 5 hours under agitation. The content of the flask were analyzed via Proton NMR, and the presence of unreacted OIP in the flask detected by this analysis indicated that the reaction was incomplete. The content of the flask were then heated to 250° C. for 3 hours under agitation until no OIP was detected. The content of the flask were analyzed via $^{31}$P-NMR, and the molar ratio of 2-isopropylphenyl dichlorophosphate to bis-(2-isopropylphenyl)chlorophosphate bis to tris-(2-isopropylphenyl)phosphate was found to be 56.2:28.7:2.8.

Example 3

Example 1 Extracted From U.S. Pat. No. 4,139,487—Comparative

Phenol (65.2 parts) and a mixture of meta- and para-isopropyl phenols (47.9 parts) were mixed with phosphorus oxychloride (51 parts; that is a 5% excess of phenolic reactants). Powdered anhydrous magnesium chloride (0.5 part) was added to catalyze the reaction. The reaction mixture was rapidly heated to 130° C. and then slowly to 230° C. over a period of about 2 hours, after which there was no further appreciable evolution of hydrogen chloride. Completion of the reaction was checked by titration tests on the crude product which was then distilled under vacuum to give a fraction of recovered phenols, a small intermediate fraction and a main ester fraction (88% of crude product) boiling at 205° C.-225° C. at 1 mm. of mercury.

The composition of the recovered phenolic fraction was shown by analysis to be substantially the same as that of the phenolic feedstock mixture, indicating that there had been no appreciable separation of the components due to preferential esterification, which was verified by hydrolyzing a portion of the main ester fraction and analyzing the recovered phenols. The distilled phosphate ester had a satisfactory color, content of oxidizable impurities and acidity and was not therefore further purified. The viscosity of the distilled phosphate ester was 30 cs at 25° C. and the specific gravity (25° C./25° C.) was 1.169. The constitution of the distilled phosphate ester is indicated in Table 2, below. The wt. % is based on the total weight of the distilled phosphate ester.

TABLE 2

| Component | wt. % |
|---|---|
| Triphenylphosphate | 30 |
| Mono-(isopropylphenyl) diphenyl phosphate | 44 |
| Bis-(isopropylphenyl) phenyl phosphate | 22 |
| Tris-(isopropylphenyl) phosphate | 4 |
| Total | 100 |

The distilled phosphate esters had a calculated carbon number of 21 and containing 33 mole-percent of the isopropylphenyl group.

Example 4

Example 2 Extracted From U.S. Pat. No. 4,139,487—Comparative

Phenol (32.6 parts) and a mixture of meta- and para-isopropyl phenols (95.8 parts) were mixed with phosphorus oxychloride (51 parts) and anhydrous magnesium chloride (0.6 part) as catalyst. Reaction and purification were carried out as in Example 1 (Example 3 herein) and the main ester fraction (89% by weight of the crude product) distilled at 207-230° C. at 1 mm of mercury. As in Example 1 (Example 3 herein) the product required no further purification and had a viscosity of 58 cs at 25° C. and a specific gravity (25° C./25° C.) of 1.123.

Analysis of the mixed ester indicated it to possess the following constitution (Table 3) (wt %). The wt. % is based on the total weight of the distilled phosphate ester.

TABLE 3

| Component | wt. % |
|---|---|
| Triphenylphosphate | 4 |
| Mono-(isopropylphenyl) diphenyl phosphate | 19 |
| Bis-(isopropylphenyl) phenyl phosphate | 52 |
| Tris-(isopropylphenyl) phosphate | 25 |
| Total | 100 |

The mixed phosphate esters had a carbon number of 24 and contained 66 mole-percent of the isopropylphenyl group.

Example 5

Unless otherwise indicated, the reactants were added to the reactor under constant agitation and the reactor's content remained under this agitation until recovery of the alkylated phenyl phosphate began. A 150 g charge of the mixture (1.1 mole of reactive isopropylated phenols prepared via ortho alkylation of phenol with propylene and $AlCl_3$), described in Table 4 below was combined with 640 g (4.17 mole) of $POCl_3$ and 1.5 grams of tetrabutyl ammonium bromide in a reactor. The mixture was heated under constant agitation to about 114° C. and refluxed at that temperature until evolution of HCl ceased, thus indicating the formation of the intermediate product. Excess $POCl_3$ was recovered from the intermediate product (95% of theoretical amount) by first heating it at atmospheric pressure to about 130° C. and then heating it to about 135° C. at 1 mmHg. Heating of the reactor's content was discontinued, the reactor's content allowed to cool, and the reactor charged with 0.3 g of $MgCl_2$ and 188 g of phenol (2.0 mole, 99.6%).

After the addition of the $MgCl_2$ and phenol, the temperature of the reactor's content was increased to about 110° C., and the reaction mixture in the reactor was then heated from about 110 to about 130° C. over a period of about 3 hours under agitation. $^{31}$P-NMR indicated complete conversion of the mono aryl dichlorophosphate and about a 55/45 mixture of the diaryl to triaryl intermediate and the alkylated triaryl phosphate ester product.

An additional 0.9 g of $MgCl_2$ was then added to the reactor and the reaction was conducted for an additional 4 hours, during which moderate HCl evolution was observed, until HCl evolution ceased. After HCl evolution ceased, 12.00 g of fresh phenol (0.13 mole, 99.6%) was charged to the reactor and the reaction was run with a nitrogen sparge at 130° C. until complete (about 2 hrs). Pressure was reduced to 10 mmHg and unreacted phenol removed overhead at 130° C. The alkylated triaryl phosphate ester thus produced was analyzed, and the alkylated triaryl phosphate ester was found to have the characteristics outlined in Table 5, below. Normalized, or relative weight percents, are based on the total weight of phenol and the alkylated triaryl phosphate ester as is indicated in the table.

TABLE 4

| $AlCl_3$ o-Alkylation IPS Mixture | | |
|---|---|---|
| Component | wt % In Crude | Normalized wt % |
| Phenol | 0.53 | 0.55 |
| OIP | 82.50 | 85.05 |
| PIP | 8.03 | 8.28 |
| 2,6-DIP | 4.87 | 5.02 |
| 2,4-DIP | 1.03 | 1.06 |
| TIP | 0.04 | 0.04 |
| Normalization Factor (%) | 97.00 | 100.00 |

TABLE 5

| Component | Formula Weight | Wt % In Crude | Normalized Wt % |
|---|---|---|---|
| TPP | 326.28 | 0.18 | 0.20 |
| 2-IPP + 3-IPP + 4-IPP | 368.36 | 84.49 | 94.39 |
| 2,4 DDP + DTPP (1) | 410.44 | 0.82 | 0.92 |
| DTPP (2,3) | 410.44 | 3.91 | 4.37 |
| TTPP | 452.52 | 0.11 | 0.12 |
| Normalization Factor | | 89.51 | 100.00 |

Example 6

Unless otherwise indicated, the reactants were added to the autoclave under constant agitation and the autoclave content remained under this agitation until recovery of the isopropylated phenols began.

A 2.0-liter Parr autoclave was charged with 50 grams of dry Amberlyst® 15 and 1200 g (12.75 mole) of molten Phenol (Mallinckrodt, 99.6% loose crystals). The autoclave was sealed, purged with $N_2$ and heated to 110° C. The headspace of the autoclave was vented to atmospheric pressure and then purged with a 10-gram charge of propylene. Propylene, 190 g (4.5 mole), was then fed to the autoclave over a 90-minute period. The feed was such that the autoclave pressure varied from 80-30 psig during the addition. The reaction temperature was maintained from 110 to 118° C. for an additional hour, and the autoclave content then cooled to 70° C. The autoclave content was then allowed to settle for 30 minutes prior to transferring (positive $N_2$ pressure through dip leg) to a nitrogen purged storage bottle.

A second 1000 g (10.6 mole) charge of molten phenol was made to the autoclave containing the IP's/Amberlyst® 15 heel. The propylation reaction was repeated with 156 g (3.7 mole) of propylene. The combined decanted reaction mixture from the first and second molten phenol additions was then fractionally distilled (1 atmosphere). The light cut (typically 93% phenol, 7% OIP) was returned to the autoclave with make-up phenol and again propylated. This decantation and distillation process was continued through 8 runs.

The concentrated crude IP's was distilled at 1 atmosphere to produce 3300 g of material. The analysis of which is reported in Table 5, below. The material was separated via distillation into a light cut (2200 g, 93% phenol and 7% OIP), which was combined with (2200 g) fresh phenol and subsequently used as the alcohol of the second step to make IPP crude in Examples 7, 8 and 10-13 below. After recovery of unreacted phenol, through the eight runs a total of 2500 g of phenol had been reacted with 1200 g of propylene to yield 3300 g of IPs suitable for use in making low TPP IPP. This material is described in Table 6 and was used as the alkylated phenol of the first step in Examples 7-13 below.

TABLE 6

| Component | Molecular Weight | IPPP Crude (wt %) |
|---|---|---|
| Phenol | 94.11 | 0.35 |
| 2-isopropylphenol (OIP) | 136.19 | 59.48 |
| 4-isopropylphenol (PIP) | 136.19 | 29.76 |
| 2,6-diisopropylphenol (2,6-DIP) | 178.27 | 4.25 |
| 2,4-diisopropylphenol (2,4-DIP) | 178.27 | 5.83 |
| 2,4,6-triisopropylphenol (2,4,6-TIP) | 220.35 | 0.32 |

Example 7

Unless otherwise indicated, the reactants were added to the reactor under constant agitation and the reactor's content remained under this agitation until recovery of the alkylated phenyl phosphate began.

A 475 g (3.34 mole of reactive isopropylated phenols) sample of the material described in Table 5, above, was combined with 795 g (5.19 mole) of $POCl_3$ and 3.56 grams (0.33 mole %) of tetrabutyl ammonium bromide. The mixture was heated to 114° C. and refluxed at that temperature until evolution of HCl slowed. The temperature was gradually increased to 135° C. and left at that temperature until HCl evolution ceased. The excess $POCl_3$ was recovered in vacuo, stripping to an end point of 135° C. and <1.0 mmHg.

After the removal of excess $POCl_3$ was complete, the reactor was allowed to cool. The reactor was then charged with 3.26 g of $MgCl_2$ (1.0 mole %) and heated to 110° C. To the reactor was fed 629.1 g (6.69 moles) of a mixture comprising phenol (96.3 wt %) and 2-isopropylphenol (3.7 wt %), recycled from the final light cut of IP's preparation described above (Example 6) with concomitant heating of the reactor's content from 110° C. to 135° C. over a 3 hour period. Within one hour after the completion of the feed, $^{31}$P-NMR analysis indicated complete conversion of the monoaryl dichlorophosphate to triaryl phosphates. The pressure was reduced to 10 mmHg and unreacted phenol partially removed overhead at 140° C.

The alkylated triaryl phosphate ester thus produced was analyzed, and the alkylated triaryl phosphate ester was found to have the characteristics outlined in Table 7, below. Normalized or relative weight percents are based on the total weight of phenol and the alkylated triaryl phosphate ester as is indicated in the table.

TABLE 7

| Major Components | Molecular Weight | Wt % In Crude | Normalized wt % |
|---|---|---|---|
| TPP | 326.28 | 0.86 | 0.98 |
| 2-IPP + 3-IPP + 4-IPP | 368.36 | 77.90 | 88.37 |
| 2,4 DDP + DTPP (1) | 410.44 | 6.50 | 7.37 |
| DTPP (2,3) | 410.44 | 2.53 | 2.87 |
| TTPP | 452.52 | 0.36 | 0.41 |
| Normalization Factor | | 88.15 | 100.00 |

Example 8

Unless otherwise indicated, the reactants were added to the reactor under constant agitation and the reactor's content remained under this agitation until recovery of the alkylated triaryl phosphate ester began.

A 470 g sample of the material described in Table 5, above, was combined with 571 g (3.73 mole) of $POCl_3$ recycled from previous Examples and 6.15 grams (0.58 mole %) of tetrabutyl ammonium bromide in a reactor. The mixture was heated to 118° C. and refluxed at that temperature until evolution of HCl slowed. The temperature was gradually increased to 135° C. and left at that temperature until HCl evolution ceased. The excess $POCl_3$ was recovered in vacuo, stripping to an end point of 135° C. and <1.0 mmHg. The reactor was allowed to cool, and then charged with 5.5 g of $MgCl_2$ (1.75 mole %) and heated to 110° C. To the reactor was fed 622.5 g (6.61 moles) of a phenol/2-isopropylphenol mixture comprising 96.3 wt % phenol and 3.7 wt % 2-isopropylphenol, with concomitant gradual increased heating from 110° to 135° C. over a 3-hour period.

Within one hour after the completion of the phenol/2-isopropylphenol mixture feed, $^{31}$P-NMR analysis indicated complete conversion of the monoaryl dichlorophosphate to triaryl phosphates. The pressure of the reactor was reduced to 10 mmHg and unreacted phenol partially removed overhead at 140° C. The alkylated triaryl phosphate ester was recovered from the reactor and analyzed, and the alkylated triaryl phosphate ester was found to have the characteristics outlined in Table 8, below. Normalized or relative weight percents are based on the total weight of phenol and the alkylated triaryl phosphate ester as is indicated in the table.

TABLE 8

| Major Components | Molecular Weight | Wt % In Crude | Normalized wt % |
|---|---|---|---|
| TPP | 326.28 | 0.58 | 0.66 |
| 2-IPP + 3-IPP + 4-IPP | 368.36 | 76.49 | 86.72 |
| 2,4 DDP + DTPP (1) | 410.44 | 7.04 | 7.98 |
| DTPP (2,3) | 410.44 | 3.35 | 3.80 |
| TTPP | 452.52 | 0.74 | 0.84 |
| Normalization Factor | | 88.20 | 100.00 |

Example 9

Unless otherwise indicated, the reactants were added to the reactor under constant agitation and the reactor's content remained under this agitation until recovery of the alkylated triaryl phosphate ester began.

A 246 g sample of the material described in Table 5, above, was combined with 800 g (5.22 mole) of POCl$_3$ and 2.56 grams (0.46 mole %) of tetrabutyl ammonium bromide. The mixture was heated to 114° C. and refluxed at that temperature until evolution of HCl slowed. The temperature was gradually increased to 135° C. and held at that temperature until HCl evolution ceased. The excess POCl$_3$ was recovered in vacuo stripping to an end point of 135° C. and <1.0 mmHg.

The reactor was allowed to cool and then charged with 2.96 g of MgCl$_2$ (1.8 mole %) and heated to 110° C. 622.5 g (6.61 moles) of Phenol (99.6%) was fed to the reactor while gradually and simultaneously increasing the temperature of the reactor's content from 110° to 135° C. over a 3-hour period. Within one hour after the completion of the feed, P-31 NMR analysis indicated complete conversion of the monoaryl dichlorophosphate to triaryl phosphates. The pressure was reduced to 10 mmHg and unreacted phenol partially removed overhead at 140° C.

The alkylated triaryl phosphate ester was recovered from the reactor and analyzed, and the alkylated triaryl phosphate ester was found to have the characteristics outlined in Table 9, below. Normalized or relative weight percents are based on the total weight of phenol and the alkylated triaryl phosphate ester as is indicated in the table.

TABLE 9

| Major Components | Molecular Weight | Wt % In Crude | Normalized wt % |
|---|---|---|---|
| TPP | 326.28 | 0.54 | 0.61 |
| 2-IPP + 3-IPP + 4-IPP | 368.36 | 80.41 | 91.23 |
| 2,4 DDP + DTPP (1) | 410.44 | 5.27 | 5.98 |
| DTPP (2,3) | 410.44 | 1.80 | 2.04 |
| TTPP | 452.52 | 0.12 | 0.14 |
| Normalization Factor | | 88.14 | 100.00 |

Example 10

Unless otherwise indicated, the reactants were added to the reactor under constant agitation and the reactor's content remained under this agitation until recovery of the alkylated triaryl phosphate ester began.

A 462 g charge of the material described in Table 5, above, was combined with 1000 g (6.52 mole) of a 1:2 mix of fresh and recycled POCl$_3$ and 3.8 grams (1.23 mole %) of MgCl$_2$. The mixture was heated initially to 85° C., and at that temperature, evolution of HCl was apparent. The temperature of the mixture was gradually increased to 135° C. and held at that temperature until HCl evolution ceased. The excess POCl$_3$ was recovered in maw, stripping to an end point of 135° C. and 50 mmHg. Toluene (2×100 g) was charged (subsurface) to the hot reactor, and the toluene was then stripped to the ending conditions of 140° C. and 50 mmHg.

The reactor was allowed to cool, and after cooling to 110° C., 612 g (6.5 moles) of a phenol/2-isopropylphenol mixture comprising 96.3 wt % phenol and 3.7 wt % 2-isopropylphenol, was fed to the reactor while gradually increasing the temperature of the reactor's content from 110° to 135° C. over a 3-hour period. Within one hour after the end of the phenol/2-isopropylphenol mixture feed, $^{31}$P-NMR analysis indicated complete conversion of the monoaryl dichlorophosphate to triaryl phosphates. The pressure of the reactor was reduced to 10 mmHg and unreacted phenol removed overhead at 140° C.

The alkylated triaryl phosphate ester was recovered from the reactor and analyzed, and the alkylated triaryl phosphate ester was found to have the characteristics outlined in Table 10, below. Normalized or relative weight percents are based on the total weight of phenol and the alkylated phenyl phosphate as is indicated in the table.

TABLE 10

| Major Components | Molecular Weight | Wt % In Crude | Normalized wt % |
|---|---|---|---|
| TPP | 326.28 | 0.73 | 0.80 |
| 2-IPP + 3-IPP + 4-IPP | 368.36 | 78.69 | 85.82 |
| 2,4 DDP + DTPP (1) | 410.44 | 7.64 | 8.33 |
| DTPP (2,3) | 410.44 | 3.97 | 4.33 |
| TTPP | 452.52 | 0.66 | 0.72 |
| Normalization Factor | | 91.69 | 100.00 |

Example 11

Unless otherwise indicated, the reactants were added to the reactor under constant agitation and the reactor's content remained under this agitation until recovery of the alkylated triaryl phosphate ester began.

A 231.5 g (1.63 mole of reactive isopropylated phenols) sample of the material described in Table 5, above, was combined with 750 g (3.01 mole) of a mix 1:2 mix of fresh and recycled POCl$_3$ and 2.6 grams (1.20 mole %) of AlCl$_3$. The mixture was heated initially to 80° C., and at that temperature, evolution of HCl was apparent. The temperature of the reactor's content was gradually increased to 135° C. and held at that temperature until HCl evolution ceased.

Excess POCl$_3$ was recovered in vacuo stripping to an end point of 135° C. and 50 mmHg. Toluene (2×100 g) was then charged (subsurface) to the hot reactor, and the toluene was then stripped to the ending conditions of 140° C. and 50 mmHg. The reactor's content was allowed to cool to 110° C., and 305 g (3.25 moles) of a phenol/2-isopropylphenol mixture comprising 96.3 wt % phenol and 3.7 wt % 2-isopropylphenol, was fed to the reactor while gradually increasing the temperature of the reactor's content from 110° C. to 135° C. over a 3-hour period. Foaming was very problematic throughout the phenol feed. Within one hour after the end of the feed, $^{31}$P-NMR analysis indicated complete conversion of the monoaryl dichlorophosphate to triaryl phosphates. The pressure was reduced to 50 mmHg and unreacted phenol partially removed overhead at 140° C.

The alkylated triaryl phosphate ester phosphate was recovered from the reactor and analyzed, and the alkylated triaryl phosphate ester was found to have the characteristics outlined in Table 11, below. Normalized or relative weight percents are based on the total weight of phenol and the alkylated triaryl phosphate ester as is indicated in the table.

TABLE 11

| Major Components | Molecular Weight | Wt % in Crude | Normalized wt % |
|---|---|---|---|
| TPP | 326.28 | 0.65 | 0.72 |
| 2-IPP + 3-IPP + 4-IPP | 368.36 | 75.00 | 82.53 |
| 2,4 DDP + DTPP (1) | 410.44 | 8.13 | 8.95 |
| DTPP (2,3) | 410.44 | 5.96 | 6.56 |
| TTPP | 452.52 | 1.14 | 1.25 |
| Normalization Factor | | 90.88 | 100.00 |

Example 12

Unless otherwise indicated, the reactants were added to the reactor under constant agitation and the reactor's content remained under this agitation until recovery of the alkylated triaryl phosphate ester began.

A 197.2 g (1.39 mole of reactive isopropylated phenols) sample of the material described in Table 5, above, was combined with 640 g (4.17 mole) of $POCl_3$ and 4.0 grams (3.64 mole %) of pyridine (dried over molecular sieves) in a reactor. The mixture was heated to 114° C. and refluxed at that temperature until evolution of HCl slowed. The temperature was then gradually increased to 135° C. with distillation of $POCl_3$ and held at that temperature until HCl evolution ceased. The remaining excess $POCl_3$ was recovered in vacuo stripping to an end point of 135° C. and 50 mmHg. During the $POCl_3$ strip, some pyridine-HCl was observed in the overhead and in the recycle $POCl_3$. Toluene (2×100 g) was charged (subsurface) to the hot reactor. Toluene was stripped to the ending conditions of 140° C. and 50 mmHg. The reactor's content was allowed to cool to 110° C., and 278 g (2.78 moles) of a phenol/2-isopropylphenol mixture comprising 96.3 wt % phenol and 3.7 wt % 2-isopropylphenol, was fed to the reactor while gradually increasing the temperature of the reactor's content from 110° to 135° C. over a 3-hour period. Within one hour after the end of the feed, $^{31}P$-NMR analysis indicated complete conversion of the monoaryl dichlorophosphate to triaryl phosphates. The pressure was reduced to 10 mmHg and unreacted phenol removed overhead at 140° C.

The alkylated triaryl phosphate ester was recovered from the reactor and analyzed, and the alkylated phenyl phosphate was found to have the characteristics outlined in Table 12, below. Normalized or relative weight percents are based on the total weight of phenol and the alkylated triaryl phosphate ester as is indicated in the table.

TABLE 12

| Major Components | FW | Wt % In Crude | Normalized wt % |
|---|---|---|---|
| TPP | 326.28 | 0.52 | 0.61 |
| 2-IPP + 3-IPP + 4-IPP | 368.36 | 76.90 | 89.53 |
| 2,4 DDP + DTPP (1) | 410.44 | 6.21 | 7.23 |
| DTPP (2,3) | 410.44 | 2.15 | 2.50 |
| TTPP | 452.52 | 0.11 | 0.13 |
| Normalization Factor | | 85.89 | 100.00 |

Example 13

Unless otherwise indicated, the reactants were added to the reactor under constant agitation and the reactor's content remained under this agitation until recovery of the alkylated triaryl phosphate ester began.

A fully jacketed 2000 ml dry round bottom flask was used as a reactor in this example. It was equipped with an overhead stirrer, thermometer, oil jacketed addition funnel and an efficient condenser/takeoff head. The reactor was vented through a Drierite® column to a caustic scrubber. 1100 g (7.17 mole) of $POCl_3$ (comprised of 2:1 mix of recycle and fresh $POCl_3$), 530 g (3.74 mole of reactive IPPs) of a mixture of isopropylated phenols comprised of 59.48 wt % OIP, 29.76 wt % PIP, 5.83 wt % 2,4-DIP and 6.0 g (2 mole % relative to reactive IPP's charged) of pyridine were charged to the reactor. The reactor's content was heated to 113° C. (oil jacket temperature 124° C.). HCl evolution initiated at 80° C. and became much more apparent at 105° C. After 90 minutes at 113° C. HCl evolution slowed. The jacket temperature was increased to 135° C., within an additional 60 minutes the pot temperature had reached 127° C., HCl Evolution was essentially complete, and pyridine.HCl separated as an oil suspended in the reaction mixture (the resulting turbidity seems to be a good visual indictor of the reaction endpoint).

The reactor jacket temperature was increased to 145° C. and the valve on the take off head was opened to the receiver, and $POCl_3$ was collected for recycle. Distillation of $POCl_3$ was facilitated with a slow nitrogen purge through the reactor headspace. Once the pot temperature reached 135° C. and $POCl_3$ distillation had slowed, the reactor pressure was gradually reduced (max vacuum 50 mmHg) until the theoretical amount of $POCl_3$ was collected (495 g, [95% of Theory] of $POCl_3$ was thus recovered). During the distillation pyridine.HCl formed in the overheads, but caused no operational problems. The last trace of $POCl_3$ was removed via the addition and stripping with 300 ml of toluene (ending conditions 135° C. 50 mmHg). An aliquot was removed for analysis; $^{31}P$-NMR analysis indicated a 97.4:2.6 relative ratio of $ArOCl_2PO:(ArO)_2ClPO$ as well as verified complete removal of $POCl_3$.

3.5 g (0.98 mole % relative to IPPs) of $MgCl_2$ were then charged to the reactor and left to stir at 140° C. under a stream of nitrogen for 1 hr. A second aliquot was removed for analysis, and $^{31}P$-NMR indicated this second aliquot had a 97.2:2.8 relative ratio of $ArOCl_2PO:(ArO)_2ClPO$. Phenol (706 g, 96.3 wt % Phenol, 3.7 wt % 2-isopropylphenol, 7.4 mole total phenols) was then charged to the oil jacketed addition funnel, from which it was gradually fed over a 75-minute period to the reactor. During this addition, HCl evolution was extremely vigorous. The reaction appeared to be complete after 170 minutes total reaction time. Conversion as measured by $^{31}P$-NMR was 99.3%. An additional 23 g charge of the phenol mixture described above was made. After an additional 30 minutes the nearly water white mixture (density=1.09, 1370 g total reaction mass, 1378 g Theory) was transferred to a wash kettle.

After the nearly water white mixture was charged to the wash kettle, 350 g of a $Na_2CO_3/HNa_2PO_4$ solution (pH=9 density=1.15) was charged to the wash kettle. The content of the wash kettle were then stirred at 88° C. for 5 minutes and then allowed to settle for a period of 20 minutes. The bottom milky (suspended $MgCO_3$) aqueous layer was removed (226 g, pH=75-8.0) from the wash kettle, and the resulting crude IPPP was washed for an additional 5 minutes with a second aliquot (90° C., 200 g) of the $Na_2CO_3/HNa_2PO_4$ solution. A second phase was removed from the bottom of the reactor to yield a 195 g less turbid yet still milky aqueous solution having a pH of 10. 530 g of a dilute $H_3PO_4$ solution, 0.56 wt %, $H_3PO_4$, based on the solution, was then charged to the reactor, and the bottom turbid product layer was collected (1357 g). The aqueous phase was removed (pH=3.5, 610 g), and the product layer was placed in a reactor and sparged with nitrogen at 95° C. to remove water, thus yielding an 1335 g of an alkylated phenyl phosphate. The alkylated triaryl phosphate ester was recovered from the reactor and analyzed, and the alkylated triaryl phosphate ester was found to have the characteristics outlined in Table 13, below. Noimalized or relative weight percents are based on the total weight of phenol and the alkylated phenyl phosphate as is indicated in the table.

TABLE 13

| Major Components | Molecular Weight | Wt % in Crude | Normalized wt % |
|---|---|---|---|
| TPP | 326.28 | 0.47 | 0.53 |
| 2-IPP + 3-IPP + 4-IPP | 368.36 | 77.51 | 87.79 |
| 2,4 DDP + DTPP (1) | 410.44 | 7.10 | 8.04 |
| DTPP (2,3) | 410.44 | 3.05 | 3.45 |
| TTPP | 452.52 | 0.16 | 0.18 |
| Normalization Factor | | 88.29 | 100.00 |

Example 14

The crude alkylated triaryl phosphate ester recovered from Examples 7-12 were combined and washed with a $Na_2CO_3/HNa_2PO_4$ having the concentrations and in the same manner described in Example 13, above. That material was then combined with the crude product from Example 13. The total mixture was then distilled under a reduced pressure (<2 mmHg) nitrogen atmosphere. During the distillation, the "forerun" (6 wt % of the total mixture, based on the mixture) was collected between 180-218° C. The "product cut" (92 wt % of the total of the total mixture, based on the mixture) was collected between 118.5-235° C. The undistilled bottoms represented the last 2 wt %, based on the mixture, of the total mass of the mixture. The forerun was analyzed by HPLC, which found 13.2 wt % phenol, 0.7 wt % 4-isopropylphenol, 13.0 wt % 2-isopropylphenol, 7.0 wt % 2,6-diisopropylphenol, 0.0 wt % TPP, 2.3 wt % monoisopropylphenyl diphenyl phosphates, 0.2 wt % diisopropylated triaryl phosphates, and 0.02 wt % triisopropylated triaryl phosphate. The product cut was also analyzed for purity and physical properties; the results are presented in the Table 14, below. All weight percents are absolute and are based on the total mass of that which is being analyzed.

TABLE 14

| Analysis HPLC | Flashed Product Wt % |
|---|---|
| Triphenyl Phosphate | 0.71 |
| Isopropylphenyl diphenyl phosphates | 87.21 |
| Diisopropylated triaryl phosphates | 11.44 |
| Triisopropylated triaryl phosphates | 0.64 |
| Acid Number | 0.11 mg KOH/g |
| APHA Color | 28.00 |
| Density (20° C.) | 1.1689 g/ml |
| Flash Point (Cleveland Open Cup) | 222° C. |
| Moisture | 19.2 ppm |
| Wt % Phosphorus (NMR) | 8.34 |
| [Al] | <0.11 ppm |
| [Mg] | <0.0018 ppm |
| [Na] | <0.6 ppm |
| Kinetic Viscosity (25° C.) | 52.91 cSt |

Thus, as illustrated in Table 14, our product, on average, is 10% higher in Phosphorous than those produced in the comparatives examples above, and is also 10% less viscous than the products of the comparative examples.

Example 15

A 5-liter reactor was equipped with an addition funnel, thermal well and distillation apparatus. The distillation apparatus was vented to a caustic scrubber through a Drierite® column. The reactor was purged with $N_2$ and charged with 3886 g (25.34 mole) of recycled $POCl_3$ and 6.37 g (0.53 mole %) of $MgCl_2$. The content of the reactor was heated to 85° C. A redistilled 67:1:32 blend (1725 g, 12.67 mole) of OIP (Aldrich)) MIP (Aldrich) and PIP (Aldrich) was fed to the reactor over a 3-hour period. During the feed the reaction temperature was gradually increased to 130° C. After 4 hours total reaction time distillation of $POCl_3$ was initiated. The reactor pressure was decreased gradually as the rate of $POCl_3$ distillation decreased. Distillation was continued to an ending condition of 140° C. and 50 mmHg. Toluene was then charged (2×250 ml) and stripped at 140° C. (50 mmHg). Phosphorus NMR of the stripped reaction mixture verified the complete removal of $POCl_3$ and indicted a 100:4.2 relative ratio of $ArOPOCl_2:(ArO)_2POCl$.

The content of the reactor was cooled to 130° C. Molten phenol (99.6%), 2362 g (25.1 mole) was feed to the reactor over a 5-hour period. Towards the end of the feed the reaction temperature was increased to 150° C. Phosphorus NMR analysis of the reactor's content confirmed complete reaction within 1-hour of the end of the feed. The content of the reactor was transferred under $N_2$ to a 5-liter storage bottle, 4547 g. HPLC analysis is Tabulated below. Normalized or relative weight percents are based on the total weight of phenol and the alkylated triaryl phosphate ester as is indicated in Table 15, below.

TABLE 15

| Major Components | Molecular Weight | Wt % In Crude | Normalized wt % |
|---|---|---|---|
| Phenol | 94.11 | 4.10 | 4.35 |
| TPP | 326.28 | 0.10 | 0.11 |
| 2-IPP + 3-IPP + 4-IPP | 368.36 | 85.90 | 91.09 |
| DTPP | 410.44 | 4.20 | 4.45 |
| TTPP | 452.52 | 0.00 | 0.00 |
| Normalization Factor | | 94.30 | |

A 5-liter glycol jacketed baffled reactor was charged with 500 g of 11% aqueous $Na_2CO_3$ and 2065 g of the alkylated triaryl phosphate ester of Table 13. The mixture was briefly stirred at 85-92° C. and then left to phase separate. The bottom aqueous layer was removed along with a clear rag layer of intermediate density. The wash procedure was repeated through 4 washes. In order to completely remove the suspended rag layer, comprised primarily of sodium and magnesium phenoxide, 2000 ml of Toluene was added. The IPP/toluene mixture was then washed with tap water (2×500 ml).

To the same 5-liter glycol jacketed baffled reactor was charged with 540 g of 4% aqueous NaOH, 2478 g of the crude product mixture and 1750 g of Toluene. The mixture was briefly stirred at 45-50° C. and then warmed to 65° C. without stirring. The resulting bottom aqueous layer was removed along with the suspended $Mg(OH)_2$ suspended within it. A second wash was conducted at 65° C. with 608 g of 1% NaOH. The product mixture was then washed at 85° C. with 532 g of tap water (resulting aqueous cut pH=10). The IPP/toluene mixture was contaminated with a fine suspension of trace $Mg(OH)_2$. This was removed by washing at 90° C. with 514 g of 0.7% $H_3PO_4$ (resulting aqueous cut pH=3.5). A final 212 g tap water wash (90° C.) resulted in an aqueous phase with pH=4.5.

The washed and stripped IPP-crude from the two separate work-up procedures above was combined. The mixture was heated to 180° C. and sparged with nitrogen to remove trace toluene, moisture and phenol. An analytical sample (500 g) was removed for the analyses reported in Table 16, below. The balance of the material was combined with the product from Example 16 and later flash distilled at 1 mmHg and 220-240° C. (see example 17 for final product analyses). All weight percents are absolute and are based on the total mass of that which is being analyzed (indicated in the table).

TABLE 16

| Analysis HPLC | Stripped Crude Product Wt % |
|---|---|
| Phenol | 0.81 |
| Triphenyl Phosphate | 0.15 |
| Isopropylphenyl diphenyl phosphates | 94.1 |
| Diisopropylated triaryl phosphates | 4.58 |
| Triisopropylated triaryl phosphates | 0.45 |
| Acid Number | 0.45 mg KOH/g |
| APHA Color | 149.00 |
| Density (20° C.) | 1.1725 g/ml |

TABLE 16-continued

| Analysis HPLC | Stripped Crude Product Wt % |
|---|---|
| Flash Point (Cleveland Open Cup) | 229° C. |
| Moisture | 46 ppm |
| Wt % Phosphorus (NMR) | 8.40 |
| [Al] | <2.0 ppm |
| [Mg] | <0.90 ppm |
| [Na] | 1.2 ppm |
| Kinetic Viscosity (25° C.) | 47.81 cSt |

Example 16

A 5-liter reactor was equipped with an addition funnel, thermal well and distillation apparatus. The distillation apparatus was vented to a caustic scrubber through a Drierite® column. The reactor was purged with $N_2$ and charged with 3385 g (22.08 mole) of recycled $POCl_3$ and 8.90 g (0.85 mole %) of $MgCl_2$. The content of the reactor was heated to 85° C. A redistilled 67:32:1 blend (1503.3 g, 11.04 mole) of OIP (Aldrich), PIP (Aldrich) and MIP (Aldrich) was fed to the reactor over a 3-hour period. During the feed the reaction temperature was gradually increased to 130° C. After 4 hours total reaction time distillation of $POCl_3$ was initiated. The reactor pressure was decreased gradually as the rate of $POCl_3$ distillation decreased. Distillation was continued to an ending condition of 150° C. and 50 mmHg. Toluene was then charged (2×250 ml) and stripped at 150° C. (50 mmHg). Phosphorus NMR of the stripped reaction mixture verified the complete removal of $POCl_3$ and indicted a 100:4 relative ratio of ArO-$POCl_2$:$(ArO)_2POCl$.

The content of the reactor was cooled to 130° C. Molten phenol (99.6%), 1984.97 g (20.75 mole) was fed to the reactor over a 5-hour period. Toward the end of the feed the reaction temperature was increased to 150° C. Phosphorus NMR analysis of the reactor's content confirmed the completion of the reaction within 1-hour of the end of the feed. The content of the reactor was transferred under $N_2$ to a 5-liter storage bottle, 3847 g. HPLC analysis of the content is in Table 175, below. Normalized or relative weight percents are based on the total weight of phenol and the alkylated triaryl phosphate ester as is indicated in the table.

TABLE 17

| Major Components | Molecular Weight | Wt % In Crude | Normalized wt % |
|---|---|---|---|
| Phenol | 94.11 | 2.29 | 2.30 |
| TPP | 326.28 | 0.15 | 0.15 |
| 2-IPP + 3-IPP + 4-IPP | 368.36 | 92.4 | 92.98 |
| DTPP | 410.44 | 4.50 | 4.53 |
| TTPP | 452.52 | 0.04 | 0.04 |
| Normalization Factor | | 99.38 | |

A 5-liter glycol jacketed baffled reactor was charged with 650 g of tap water, 1750 ml of toluene and 1915 g of the crude product mixture of Table 15. The mixture was briefly stirred at from 85 to 92° C. and then left to phase separate. The bottom aqueous layer was removed along with a turbid rag layer of intermediate density. The organic layer was washed (2×1000 g) with 2% aqueous NaOH at 85° C. and then washed (4×800 g) with tap water until a neutral pH of the wash water was achieved. The above process was repeated with the balance of the crude material (1897 g). The washed crude product mixtures were combined and transferred to a third reactor where toluene, and moisture were removed in vacuo, ending conditions 180° C. and 1 mmHg. An analytical sample was found to have the characteristics listed in Table 18, below. All weight percents are absolute and are based on the total mass of that which is being analyzed. The balance of the material left after analysis was combined with the product from Example 15 and later flash distilled at 1 mmHg and 220-240° C. (see Example 17 for final product analyses).

TABLE 18

| Analysis HPLC | Stripped Crude Product Wt % |
|---|---|
| Phenol | 407 ppm |
| Triphenyl Phosphate | 0.16 wt % |
| Isopropylphenyl diphenyl phosphates | 94.6 wt % |
| Diisopropylated triaryl phosphates | 4.6 wt % |
| Triisopropylated triaryl phosphates | 0.01 wt % |
| Acid Number | 0.05 mg KOH/g |
| APHA Color | 221 |
| Wt % Phosphorus (NMR) | 8.32 |
| [Al] | <3.6 ppm |
| [Mg] | 1.41 ppm |
| [Na] | 1.68 ppm |

Example 17

The stripped crude product mixtures from Examples 15 and 16 were combined and flash distilled at from 220 to 240° C. and vacuum of <1 mmHg. The product thus obtained had the characteristics presented in the Table 19, below. All weight percents are absolute and are based on the total mass of that which is being analyzed in the Table.

TABLE 19

| Analysis HPLC | Flashed Product Wt % |
|---|---|
| Phenol | 200 ppm |
| Triphenyl Phosphate | 0.17 |
| Isopropylphenyl diphenyl phosphates | 94.93 |
| Diisopropylated triaryl phosphates | 4.87 |
| Triisopropylated triaryl phosphates | 0.02 |
| Acid Number | 0.03 mg KOH/g |
| APHA Color | 27.00 |
| Density (20° C.) | 1.1729 g/ml |
| Flash Point (Cleveland Open Cup) | 236° C. |
| Moisture | 24 ppm |
| Wt % Phosphorus (NMR) | 8.36 |
| [Al] | <0.1 ppm |
| [Mg] | <0.06 ppm |
| [Na] | <0.56 ppm |
| Kinetic Viscosity (25° C.) | 48.74 cSt |

Example 18

A 5-liter reactor was equipped with an addition funnel, thermal well and distillation apparatus. The distillation apparatus was vented to a caustic scrubber through a Drierite® column. The reactor was purged with $N_2$ and charged with 900.00 g (5.88 mole) of recycled $POCl_3$ 21.0 g (3.94 mole %) of dry pyridine and 916.1 g (6.73 mole) of the redistilled 67:32:1 blend of OIP (Aldrich), PIP (Aldrich) and MIP (Aldrich). The stirred content of the reactor was heated to 114° C., the temperature at which HCl evolution began in earnest. During the course of 7 hours the reaction temperature was gradually increased to 130° C. After 8 hours of total reaction time a sample was removed and analyzed by Phosphorus NMR, which indicted a 93.6:18.5 relative ratio of ArOPOCl$_2$: $(ArO)_2POCl$.

The content of the reactor was left to stand overnight and then again heated to 130° C. with stirring. Molten phenol (99.6%), 996.46 g (10.59 mole) was fed to the reactor over a 5-hour period. Toward the end of the feed the reaction temperature was increased to 170° C. Phosphorus NMR analysis of the reactor's content confirmed complete reaction within 3-hours after the end of the feed. The content of the reactor was transferred under $N_2$ to a 5-liter storage bottle, 2055 g. HPLC analysis indicated it had the properties set out in Table 20, below. Normalized or relative weight percents are based on the total weight of phenol and the alkylated phenyl phosphate as is indicated in the table.

TABLE 20

| Major Components | Molecular Weight | Wt % in Crude | Normalized wt % |
|---|---|---|---|
| Phenol | 94.11 | 2.08 | 2.09 |
| TPP | 326.28 | 0.13 | 0.13 |
| 2-IPP + 3-IPP + 4-IPP | 368.36 | 70.33 | 70.83 |
| DTPP | 410.44 | 26.16 | 26.35 |
| TTPP | 452.52 | 0.59 | 0.59 |
| Normalization Factor | | 99.29 | |

A 5-liter glycol jacketed baffled reactor was charged with 650 g of tap water, 1750 ml of toluene and 2055 g of the crude product mixture. The mixture was briefly stirred at from 85 to 92° C. and then left to phase separate. The bottom aqueous layer was removed along with a turbid rag layer of intermediate density. The organic layer was washed (2×1000 g) with 2% aqueous NaOH at 85° C. and then washed (4×800 g) with tap water until a neutral pH of the wash water was achieved. The washed crude product mixtures were then transferred to a third reactor where toluene, moisture and phenols were removed in vacuo, ending conditions 180° C. and 1 mmHg. An analytical sample was removed and characterized. The results are reported in the Table 21, below. All weight percents are absolute and are based on the total mass of that which is being analyzed in the Table.

TABLE 21

| Analysis HPLC | Flashed Product Wt % |
|---|---|
| Phenol | 0.07 |
| Triphenyl Phosphate | 0.14 |
| Isopropylphenyl diphenyl phosphates | 72.2 |
| Diisopropylated triaryl phosphates | 27.0 |
| Triisopropylated triaryl phosphates | 0.61 |
| Acid Number | 0.01 mg KOH/g |
| APHA Color | 92 |
| Wt % Phosphorus (NMR) | 8.1% |

The balance of the material in the reactor was flash distilled at 1 mmHg and 220-240° C. The product thus obtained was analyzed and found to exhibit the characteristics presented in Table 22, below. All weight percents are absolute and are based on the total mass of that which is being analyzed in the Table.

TABLE 22

| Analysis HPLC | Flashed Product Wt % |
|---|---|
| Phenol | <100 ppm |
| Triphenyl Phosphate | 0.14 |
| Isopropylphenyl diphenyl phosphates | 72.16 |
| Diisopropylated triaryl phosphates | 27.10 |
| Triisopropylated triaryl phosphates | 0.61 |
| Acid Number | <0.01 mg KOH/g |
| APHA Color | 35 |
| Density (20° C.) | 1.1631 |
| Wt % Phosphorus (NMR) | 8.22% |
| Kinetic Viscosity (25° C.) | 55.80 cSt |

Example 18

Several test formulations were prepared by combining the materials outlined below in the amounts described below. Each formulation was prepared by mixing the components in a #5 Brabender bowl at 160-165° C. and compression molded at 165° C. into the appropriate thickness test specimens. ASTM type IV tensile bars were die cut from compression-molded plaques at 1/16" thickness. All formulations are based on a 75 Shore A hardness, 60° C. flexible PVC formulation. Resin molecular weight is suitable for thick wall injection molding or thin wall profile or wire extrusion or film. Each test formulations contained the following:

Component Amounts in Formulation

| | |
|---|---|
| Oxy 226 PVC Resin | 100 |
| Flame Retardant | 55 |
| Drapex 6.8 Epoxidized Soybean Oil | 6 |
| Mark 4782A Ba/Zn Heat Stabilizer | 2.5 |
| Stearic Acid | 0.25 |
| Total | 163.75 |

Flame Retardants Evaluated

TS-06-9A—Antiblaze® 519

TS-06-9B—Chemtura Reofos 50®

TS-06-9C—Supresta™ Phosflex 31L

TS-06-9D—Flame Retardant According to the Present Invention

TS-06-9E—Flame Retardant According to the Present Invention

TS-06-9F—Flame Retardant According to the Present Invention

TABLE 23

MECHANICAL, ELECTRICAL AND COMPATIBILITY RESULTS IN 75 SHORE A FLEXIBLE PVC

| | TS-06- | | | | | |
|---|---|---|---|---|---|---|
| Test | 9A | 9B | 9C | 9D | 9E | 9F |
| Hardness Shore A Inst/15 sec. 1/4" Thick | 85/76 | 82/74 | 84/78 | 83/76 | 84/77 | 84/77 |
| Specific Gravity | 1.30 | 1.29 | 1.29 | 1.29 | 1.28 | 1.28 |
| Tensile Strength 1/16" Thick, psi | 3100 | 3050 | 3020 | 2980 | 3020 | 3000 |
| 100% Modulus, psi | 2010 | 1920 | 1920 | 1810 | 1850 | 1930 |

TABLE 23-continued

MECHANICAL, ELECTRICAL AND COMPATIBILITY RESULTS IN 75 SHORE A FLEXIBLE PVC

| | TS-06- | | | | | |
|---|---|---|---|---|---|---|
| | 9A | 9B | 9C | 9D | 9E | 9F |
| 200% Modulus, psi | 2860 | 2810 | 2710 | 2600 | 2670 | 2710 |
| Elongation @ Break 1/16" Thick, % | 240 | 250 | 260 | 270 | 260 | 260 |
| Aged 7 days @ 100° C. | | | | | | |
| Tensile Retention % | 103 | 107 | 108 | 109 | 106 | 100 |
| Elongation Retention % | 54 | 46 | 55 | 67 | 75 | 60 |
| Limiting Oxygen Index, % $O_2$ | 32.2 | 32.3 | 32.0 | 31.6 | 31.8 | 32.2 |
| Volume Resistivity @ 23° C., Ω · cm | 3.6E12 | 2.5E12 | 2.9E12 | 3.2E12 | 3.5E12 | 3.5E11 |
| Loop Spew, 1/16" thick, 1" loop | None | None | None | None | None | None |
| Clarity, 1/4" thick | Good | Good | Good | Good | Good | Good |
| Yellowness Index, 1/4" thick | 16.6 | 20.0 | 17.8 | 15.8 | 16.1 | 22.6 |
| Haze, 1/4" thick | None | None | None | None | None | None |
| High Humidity Exudation, 72 hours @ 80° C. | | | | | | |
| Tack | Slight | Slight | Slight | V. Slight | Slight | V. Slight |
| Haze | High | High | High | High | High | High |
| Color Development | None | Slight Yellow | None | None | None | None |

The invention claimed is:

1. A process for making alkylated triaryl phosphate esters comprising:
   a) reacting an alkylated phenol stream comprising less than about 1 mole % phenol and up to about 25 mole % dialkyl phenol, both based on the total weight of the alkylated phenol, with $POCl_3$ in the presence of a first catalyst under first reaction conditions, including temperatures ranging from about 80° C. to about 210° C., thereby producing a first reaction product comprising greater than about 75 mole % monoalkylated phenyl-dichloro phosphates, based on the total moles of the first reaction product, and wherein said first reaction product is:
      i) reacted with an alcohol selected from aryl alcohols, alkyl alcohols, alkylated aryl alcohols, and mixtures thereof in the presence of a second catalyst under second reaction conditions including temperatures ranging from about 90° C. to about 260° C. thereby producing an alkylated triaryl phosphate ester; or
      ii) sequentially reacted with more than one alcohol selected from aryl alcohols, alkyl alcohols, alkylated aryl alcohols, and mixtures thereof in the presence of a second catalyst under second reaction conditions including temperatures ranging from about 70° C. to about 260° C. thereby producing an alkylated triaryl phosphate ester; or
      iii) reacted with a first alcohol thereby producing a partially reacted product, and reacting the partially reacted product with a second alcohol, wherein the second alcohol is not added until the first alcohol has been consumed, as determined by a suitable method such as $P^{31}NMR$, wherein said first alcohol and said second alcohol are independently selected from aryl alcohols, alkyl alcohols and alkylated aryl alcohols thereby producing an alkylated triaryl phosphate ester.

2. The process according to claim 1 wherein the alkyl moieties of the alkylated phenol are independently selected from methyl, ethyl, propyl, isopropyl, butyl, isobutyl, tertiary-butyl, amyl, isoamyl, tertiary-amyl groups, cyclohexyl alkyl moieties, isopropyl alkyl, and combinations thereof.

3. The process according to claim 1 wherein the alkyl moieties of the alkylated phenol are isopropyl alkyl moieties.

4. The process according to claim 1 wherein the alkylated phenol stream comprises in the range of from about 64 to about 68 wt. % ortho-isopropylphenol, in the range of from about 0.5 to about 2.5 wt. % meta-isopropylphnenol, and in the range of from about 31 to about 35 wt. % para-isopropylphenol, all based on the total weight of the alkylated phenol.

5. The process according to claim 1 wherein the first reaction product comprises in the range of from about 70 to about 99.9 mole % monoalkylated phenyl-dichloro phosphates and in the range of from about 0.1 mole % but less than 30 mole %, bis-(monoalkylated)phenyl-chloro phosphates, both based on the total moles of the first reaction product excluding unreacted $POCl_3$.

6. The process according to claim 1 wherein said process further comprises:
   a) adding to the alkylated triaryl phosphate ester an additional amount of alcohol selected from monoisopropylated phenols, diisopropylated phenols, phenol, and mixtures thereof, and/or an additional amount of second catalyst to the alkylated triaryl phosphate ester, thus producing an alcohol-rich alkylated phenyl phosphate product containing excess alcohol;
   b) recovering said alcohol-rich alkylated phenyl phosphate product; and
   c) removing at least a portion of the excess alcohol from the alcohol-rich alkylated phenyl phosphate ester product; wherein the excess alcohol is removed by a method selected from phase separation, stripping, distillation, and mixtures thereof.

7. The process according to claim 1 wherein said process further comprises i) dividing said first alcohol into a first and second portion; ii) reacting the first reaction product with the first portion of the first alcohol until substantially all of the first portion of the first alcohol is consumed, as determined by a suitable method such as $P^{31}NMR$; adding the second portion of the first alcohol; reacting the product from ii) with the second portion of the first alcohol until substantially all of the second portion of the first alcohol has been consumed, as determined by a suitable method such as $P^{31}NMR$, thus producing a first intermediate reaction product comprising at least aryl dichlorophosphate and chloro diarylphosphate; iii) reacting the first intermediate reaction product with an effective amount of the second alcohol.

8. The process according to claim 7 wherein said effective amount of the second alcohol is that amount of the second alcohol that is effective at converting substantially all of the aryl dichlorophosphate and chloro diarylphosphate to alkylated triaryl phosphate.

* * * * *